US009634734B2

(12) United States Patent
Lee et al.

(10) Patent No.: US 9,634,734 B2
(45) Date of Patent: Apr. 25, 2017

(54) IMPLANTABLE MEDICAL DEVICE AND POWER CONTROLLING METHOD THEREOF

(75) Inventors: Ki-Won Lee, Pyeongtaek-si (KR); Hoseung Lee, Pyeongtaek-si (KR); Se-Ik Park, Pyeongtaek-si (KR)

(73) Assignee: ALPINION MEDICAL SYSTEMS CO., LTD. (KR)

( * ) Notice: Subject to any disclaimer, the term of this patent is extended or adjusted under 35 U.S.C. 154(b) by 368 days.

(21) Appl. No.: 14/122,575

(22) PCT Filed: Oct. 27, 2011

(86) PCT No.: PCT/KR2011/008087
§ 371 (c)(1),
(2), (4) Date: Mar. 14, 2014

(87) PCT Pub. No.: WO2012/165725
PCT Pub. Date: Dec. 6, 2012

(65) Prior Publication Data
US 2014/0194058 A1  Jul. 10, 2014

(30) Foreign Application Priority Data
May 27, 2011  (KR) .................. 10-2011-0050894

(51) Int. Cl.
*H04B 7/00* (2006.01)
*H04B 5/00* (2006.01)
(Continued)

(52) U.S. Cl.
CPC ......... *H04B 5/0037* (2013.01); *A61N 1/3787* (2013.01); *H02J 7/025* (2013.01);
(Continued)

(58) Field of Classification Search
CPC .............. A61M 1/127; A61M 2205/04; A61M 2205/3523; A61M 2205/8243;
(Continued)

(56) References Cited

U.S. PATENT DOCUMENTS 7,657,320 B2  2/2010  Chadwick
2002/0177884 A1  11/2002  Ahn et al.
(Continued)

FOREIGN PATENT DOCUMENTS

CN  101352596 A  1/2009
KR  10-2002-0089605 A  11/2002
(Continued)

OTHER PUBLICATIONS

International Search Report (in Korean with English translation) for PCT/KR2011/008087, mailed May 31, 2012; ISA/KR.

*Primary Examiner* — Xin Jia
(74) *Attorney, Agent, or Firm* — Harness, Dickey & Pierce, P.L.C.

(57) ABSTRACT

An implantable medical device includes a secondary coil for receiving an RF signal from the external terminal by an induced electromotive force excited by an external terminal primary coil. RF signal includes a power signal for energizing the medical device and data signal generated upon modulation of the power signal for use in controlling the medical device. The implantable medical device further comprises: a power processing block for converting the received power signal into DC for use by the implantable medical device; a data communication circuit activated by the DC supplied from the power processing block for demodulating the modulated data signal from the RF signal; a charge unit for charging a battery with the DC supplied from the power processing block; and a control unit to be operative by a power supply from the battery for controlling
(Continued)

the implantable medical device according to the demodulated data signal.

8 Claims, 2 Drawing Sheets

(51) Int. Cl.
| | | |
|---|---|---|
| *A61N 1/378* | (2006.01) | |
| *H02J 7/02* | (2016.01) | |
| *H02J 17/00* | (2006.01) | |
| *H02J 50/10* | (2016.01) | |
| *H02J 50/80* | (2016.01) | |
| *A61M 1/12* | (2006.01) | |

(52) U.S. Cl.
CPC .............. *H02J 17/00* (2013.01); *H02J 50/10* (2016.02); *H02J 50/80* (2016.02); *H04B 5/0093* (2013.01); *A61M 1/127* (2013.01); *A61M 2205/04* (2013.01); *A61M 2205/3523* (2013.01); *A61M 2205/8243* (2013.01)

(58) Field of Classification Search
CPC ........ A61N 1/3787; H02J 17/00; H02J 7/025; H04B 5/0037; H04B 5/0093
See application file for complete search history.

(56) References Cited

U.S. PATENT DOCUMENTS

| | | |
|---|---|---|
| 2005/0162125 A1 | 7/2005 | Yu et al. |
| 2005/0288743 A1 | 12/2005 | Ahn et al. |
| 2008/0039903 A1 | 2/2008 | Chadwick |
| 2009/0048643 A1* | 2/2009 | Erickson ................. A61N 1/378 607/59 |
| 2009/0082705 A1* | 3/2009 | Asfora ................... A61H 19/00 601/46 |
| 2010/0007307 A1 | 1/2010 | Baarman et al. |
| 2010/0292050 A1* | 11/2010 | DiBenedetto ...... A63B 24/0062 482/9 |
| 2011/0316476 A1* | 12/2011 | Washiro .................. H02J 7/025 320/108 |
| 2012/0256492 A1* | 10/2012 | Song ....................... H02J 1/102 307/66 |
| 2012/0299389 A1* | 11/2012 | Lee ...................... H04B 5/0031 307/104 |

FOREIGN PATENT DOCUMENTS

| | | |
|---|---|---|
| KR | 10-2007-0021071 A | 2/2007 |
| KR | 10-2011-0034664 A | 4/2011 |

* cited by examiner

IMPLANTABLE MEDICAL DEVICE AND POWER CONTROLLING METHOD THEREOF

TECHNICAL FIELD

The present disclosure in some embodiments relates to an implantable medical device. More particularly, the present disclosure relates to an implantable medical device which can be awakened to a power signal and a power controlling method thereof.

BACKGROUND

The statements in this section merely provide background information related to the present disclosure and may not constitute prior art.

As is known, an implantable pulse generator, a cochlear implant, a deep brain stimulator, and such medical devices that are inserted into the body of human, animal, etc. maintain communication and power transfer with external devices by magnetic coupling for establishing a low-frequency magnetic field by using an inductive link coil. In particular, communication data and electric power are transferred from the external device to the implantable medical device by an induced electromotive force between a primary coil of the external device and a secondary coil of the implantable medical device. The implantable medical device having a secondary coil is configured with dozens of circuit components which respectively need power consumption to perform their assigned functions.

Here, each of the circuit components may be divided into a data communication section and an operative section. Medical devices have a rechargeable internal battery for supplying electric power to the respective circuit components.

In general, the implanting nature of such medical device inevitably limits the overall device size which in turn restricts the maximum allowable dimension of the battery to be employed. The limited battery capacity generally proportional to the small size results in undersized and low-capacity implantable medical devices which suffer from frequent recharging. This is the major factor in diminishing the usability of the implantable medical devices.

Therefore, a low power system for implantable medical devices is needed in practice for reducing the power consumption of the device components to the minimum by securing the most battery capacity available.

DISCLOSURE

Technical Problem

Some embodiments of the present disclosure provide implantable medical devices rechargeable with an RF signal and a power controlling method thereof.

Some embodiments of the present disclosure provide implantable medical devices which can be awakened by RF signal and a power controlling method thereof.

SUMMARY

At least one embodiment of the present disclosure provides an implantable medical device interworking with an external terminal having a primary coil, including a secondary coil configured to receive an RF signal from the external terminal by an induction of an induced electromotive force between the primary coil and the secondary coil, the RF signal including a power signal for energizing the implantable medical device and a data signal generated upon modulation of the power signal for use in controlling the implantable medical device. The implantable medical device further includes a power processing block, a data communication circuit, a charge unit and a control unit. The power processing block is configured to convert the power signal into a DC (direct current) power to be used by the implantable medical device. The data communication circuit is configured to be activated by the DC power supplied from the power processing block and to demodulate the modulated data signal from the RF signal. The charge unit is configured to charge a battery with the DC power supplied from the power processing block. And the control unit is configured to be operated by an operation power supplied from the battery and to control the implantable medical device according to the demodulated data signal.

Another embodiment of the present disclosure provides a power control method for an implantable medical device comprising converting an RF signal induced between a primary coil on an external terminal and a secondary coil on the implantable medical device into a DC power to be used by the implantable medical device; and supplying the converted DC power to a data communication circuit for performing a data communication with the external terminal.

Yet another embodiment of the present disclosure provides an implantable medical device interworking with an external terminal having a primary coil, including: a secondary coil configured to receive an RF signal from the external terminal by an induction of an induced electromotive force between the primary coil and the secondary coil, the RF signal including a power signal for energizing the implantable medical device and a data signal generated upon modulation of the power signal for use in controlling the implantable medical device. The implantable medical device further includes: a power processing block, a charge unit, a communication signal detector, a data communication circuit, and a control unit. The power processing block is configured to convert the received power signal into a DC power to be used by the implantable medical device. The charge unit is configured to charge a battery with the DC power supplied. The communication signal detector is configured to detect the data signal from the power signal. The data communication circuit is configured to be energized by the DC power supplied from the power processing block while the data signal is detected and to demodulate the modulated data signal. And the control unit is configured to be energized by an operation power supplied from the battery, to control the implantable medical device according to the demodulated data signal, and to selectively connect or disconnect the power supply from the battery depending on the presence of the data signal detected by the communication signal detector.

Yet another embodiment of the present disclosure provides a power control method of an implantable medical device, the power controlling method including detecting an RF signal induced from a primary coil provided at an external terminal to a secondary coil provided at the implantable medical device, the RF signal including a power signal for energizing the implantable medical device and a data signal generated upon modulation of the power signal for use in controlling the implantable medical device. The power controlling method further includes supplying a control unit, in response to a detection of the data signal, with an operation power from a battery of the implantable medical device and supplying a data communication circuit for communicating with the external terminal with a DC power from a power processor after a conversion from the RF signal. The power controlling method further includes cutting off a power supply to the control unit and the data communication circuit in the absence of the detection of the data signal.

DETAILED DESCRIPTION

Figure 1:
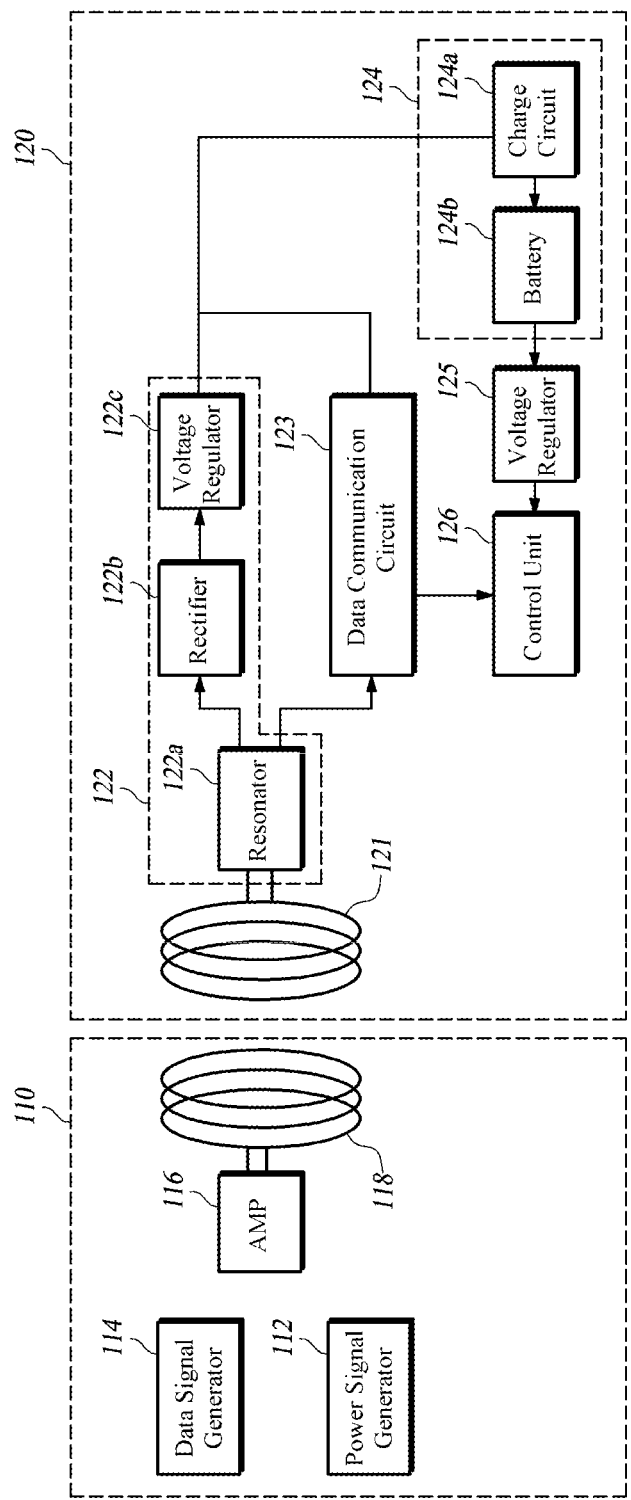
FIG. 1 is a block diagram of an implantable medical system for illustrating an implantable medical device communicating with an external terminal according to at least one embodiment.

Hereinafter, some embodiments of the present disclosure will be described in detail with reference to the accompanying drawings. In the following description, like reference numerals designate like elements although the elements are shown in different drawings.

FIG. 1 is a block diagram of an implantable medical system for illustrating an implantable medical device communicating with an external terminal according to at least one embodiment.

As shown in FIG. 1, an external terminal 110 supplies a power signal to an implantable medical device 120 in a non-contact manner. The electric power for use in the implantable medical device 120 includes a charging power for a battery within the implantable medical device and an operation power for a data communication circuit within the implantable medical device.

The external terminal 110 includes a power signal generator 112, a data signal generator 114, an amplifier 116 and a primary coil 118.

First, the power signal generator 112 generates the power signal for energizing the implantable medical device 120, for example, a power signal with a rectangular waveform having a frequency on the order of several MHz. The power signal generated by the power signal generator 112 is provided to the power amplifier 116.

The data signal generator 114 generates a low frequency signal used for the operation of the implantable medical device 120, for example, a data signal with a rectangular waveform having a frequency of several dozen to several hundred kHz. The data signal of the low frequency generated by the data signal generator 114 is provided to the power amplifier 116.

The power amplifier 116 generates a sinusoidal waveform corresponding to the power signal of the rectangular wave provided from the power signal generator 112 and amplitude-modulates the sinusoidal waveform with the data signal to generate an RF signal to be transferred to the implantable medical device 120. In the power amplifier 116, the sinusoidal waveform is used as a carrier, which is modulated with the data signal from the data signal generator 114. Therefore, a power signal and a data signal are included in the RF signal. In the present embodiment, the power amplifier 116 is implemented with a Class-E power amplifier.

The primary coil 118 generates magnetic field in response to the RF signal from the power amplifier 116. When the external terminal 110 and the implantable medical device 120 approach each other within a proximity distance, the primary coil 118 produces an induced electromotive force in a secondary coil 121 provided at the implantable medical device 120.

Further, the implantable medical device 120 according to the present disclosure includes the secondary coil 121, a power processing block 122, a data communication circuit 123, a charge unit 124, a voltage regulator 125 and a control unit 126. For example, the implantable medical device 120 may include, but not limited to, an implantable pulse generator, a cochlear implant and a deep brain stimulator.

The power processing block 122 generates a charging power or an operation power necessary for the implantable medical device from the induced electromotive force by the induction to the secondary coil 121. The power processing block 122 includes a resonator 122a configured to generate an RF signal of a particular frequency band from the induced electromotive force excited in the secondary coil 121, a rectifier 122b configured to rectify the generated RF signal of a sinusoidal waveform into a DC electric power, a data communication circuit 123 configured to demodulate a modulated data signal from the RF signal and provide a demodulated data signal to the control unit 126, and a regulator 122c configured to regulate the rectified DC power and provide the regulated DC power to the data communication circuit 123 and the charge unit 124.

The data communication circuit 123 operates during a communication with the external terminal 110 and may be less frequently used than the control unit 126. With this point in view, embodiments of the present disclosure are implemented not to supply the DC power from the power processing block 122 to the data communication circuit 123 unless magnetic coupling occurs in the secondary coil 121, but to supply the DC power straight from the power processing block 122 for communicating data with the external terminal 110 only when magnetic coupling occurs between the primary coil 118 and the secondary coil 121. The charge unit 124 includes a charge circuit 124a and a battery 124b, and the charge circuit 124a charges the battery 124b by using a DC power provided from the power processing block 122.

The regulator 125 is disposed between the charge unit 124 and the control unit 126 to regulate the operation power provided by the battery 124b and provide the regulated operation power to the control unit 126.

The control unit 126 is provided with energy by the operation power from the battery 124b to perform main functions, such as a heart stimulating operation of an implantable pulse generator, a nerve stimulating operation of a cochlear implant, and a brain stimulating operation of a deep brain stimulator, according to a data signal provided by the data communication circuit 123.

Figure 2:
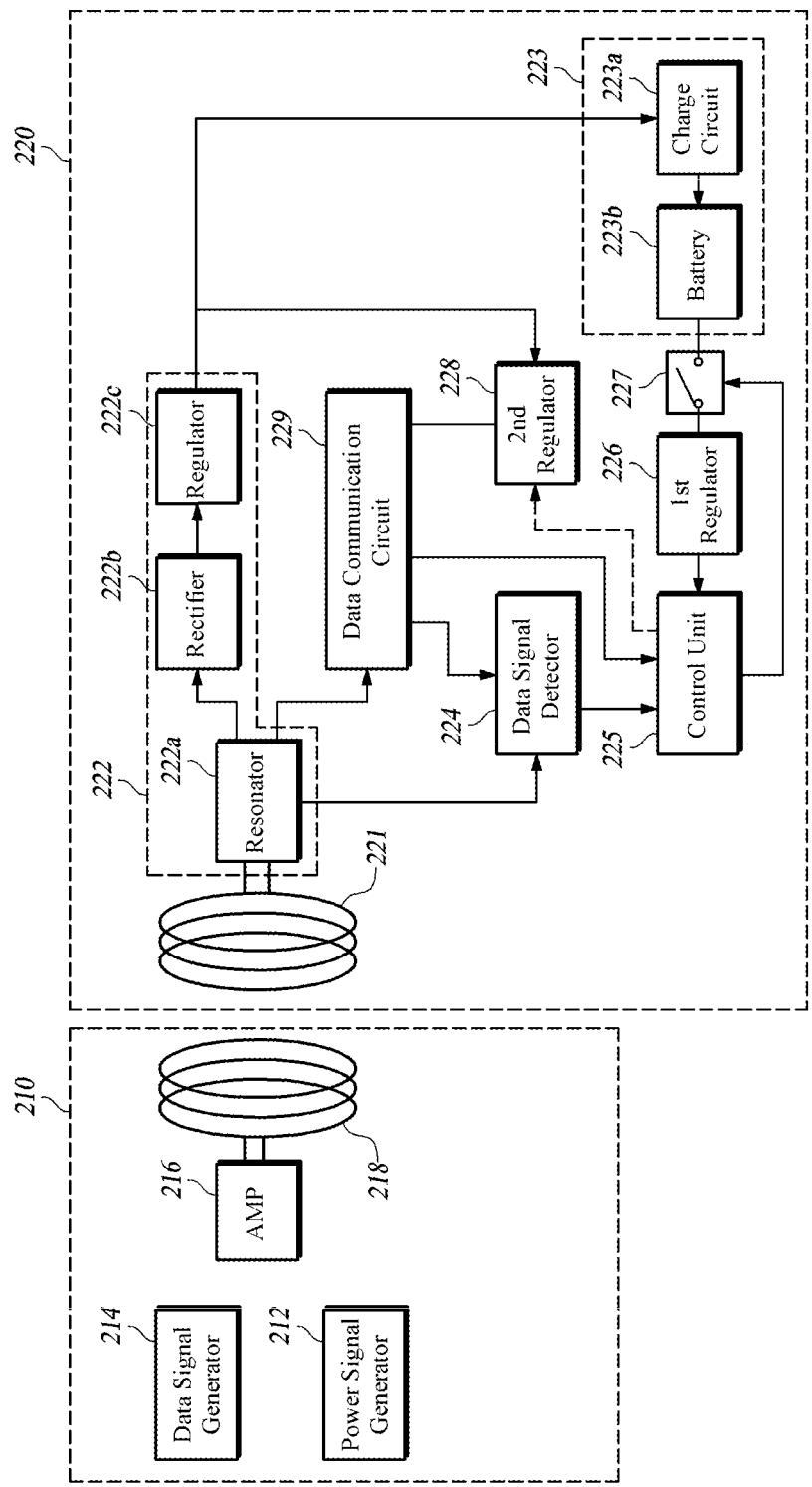
FIG. 2 is a block diagram of an implantable medical system for illustrating an implantable medical device communicating with an external terminal according to another embodiment.

FIG. 2 is a block diagram of an implantable medical system for illustrating an implantable medical device communicating with an external terminal according to another embodiment.

As shown in FIG. 2, an external terminal 210 supplies a power signal used for generating an electric power to an implantable medical device 220 in a non-contact manner. The source of the electric power used by the implantable medical device 220 includes the source of a charging power for a battery within the implantable medical device and that of an operation power for a data communication circuit within the implantable medical device, as described below.

The external terminal 210 includes a power signal generator 212, a data signal generator 214, a power amplifier 216, and a primary coil 218.

The power signal generator 212 generates a power signal for energizing the implantable medical device 220, for example, a power signal with a rectangular waveform having a frequency of several MHz. The power signal generated by the power signal generator 212 is provided to the power amplifier 216.

The data signal generator 214 generates a low frequency signal required for the operation of the implantable medical device 220, for example, a data signal having a frequency of several dozens to several hundreds of kHz, and the generated low frequency signal is provided to the power amplifier 216.

The power amplifier 216 generates a sinusoidal waveform corresponding to the power signal of the rectangular wave provided from the power signal generator 212 and amplitude-modulates the data signal of the sinusoidal waveform generated by the data signal generator 214 to generate an RF signal. In the power amplifier 216, the sinusoidal wave is used as a carrier which is amplitude-modulated with the data signal. Therefore, a power signal and a data signal are carried by the RF signal. In the present embodiment, the power amplifier 216 may be implemented with a Class-E power amplifier.

The primary coil 218 generates a magnetic field in response to the RF signal from the power amplifier 216. When the external terminal 210 and the implantable medical device 220 approach each other within a proximity distance, the primary coil 218 induces an induced electromotive force on a secondary coil 221 provided at the implantable medical device 220.

Further, the implantable medical device 220 includes the secondary coil 221, a power processing block 222, a charge unit 223, a communication signal detector 224, a control unit 225, a first regulator 226 for regulating voltage, a switch 227, a second regulator 228 and a data communication circuit 229. The implantable medical device 220 may include, but is not limited to, an implantable pulse generator, a cochlear implant and a deep brain stimulator. The power processing block 222 generates a charging power or an operation power necessary for the implantable medical device 220 from the induced electromotive force by the excitation by the secondary coil 221. The power processing block 222 includes a resonator 222a configured to generate an RF signal of a particular frequency band from the induced electromotive force, a rectifier 222b configured to rectify the sinusoidal waveform of the generated RF signal into a DC electric power, a data communication circuit 229 configured to demodulate a modulated data signal from the RF signal to provide a demodulated data signal to the control unit 225, and a regulator 222c configured to regulate the rectified DC power and provide the regulated DC power to the charge unit 223 and the second regulator 228.

The charge unit 223 includes a charge circuit 223a and a battery 223b. The charge circuit 223a charges the battery 223b with the DC power provided from the power processing block 222.

The control unit 225 is powered by the operation power supplied from the battery 223b and performs main functions, such as a heart stimulating operation of an implantable pulse generator, a nerve stimulating operation of a cochlear implant, and a brain stimulating operation of a deep brain stimulator, according to a data signal provided by the data communication circuit 229. Further, when the control unit 225 receives a shutdown mode entry command included in a data signal and no data signal is detected by the communication signal detector 224, it performs control to interrupt the supply of the operation power to the related elements including the control unit 225 itself. In embodiments of the present disclosure, this state is referred to as a shutdown mode in which all the elements in the implantable medical device maintain turnoff state.

The implantable medical device 220 further includes the first regulator 226 and the switch 227 arranged between the control unit 225 and the charge unit 223.

The first regulator 226 regulates the operation power provided by the battery 223b and provides the regulated operation power to the control unit 225.

The switch 227 is selectively turned on/off pursuant to the control by the control unit 225. Such a selective on/off operation of the switch 227 may either supply or shut off the operation power of the battery 223b provided to the control unit 225. The second regulator 228 regulates the DC power provided by the regulator 222c and supplies or interrupts the regulated DC power as an operation power to the data communication circuit 229. For example, when a data signal is detected by the communication signal detector 224, the second regulator 228 is enabled under the control of the control unit 225 to allow the DC power from the regulator 222c to energize the communication circuit 229. In contrast, when a data signal is not detected by the communication signal detector 224, the second regulator 228 may be disabled under the control of the control unit 225 to interrupt the supply of the DC power from the regulator 222c.

The reason why the embodiment shown in FIG. 2 employs a separate second regulator 228 is that it is different from the embodiment shown in FIG. 1 in which an electric power signal having an AC waveform enables supply of an electric power to a data communication circuit even without a data signal. The operation scheme of shutting off power supply to the data communication circuit 229 when the AC waveform of power signal is used only for charging purpose and in the absence of detected data signal as the embodiment shown in FIG. 2. The data communication circuit 229 operates during a communication with the external terminal 210 and may be thus less frequently used than the control unit 225. Therefore, in the present embodiment reflecting this point, the operation power from the regulator 222c is not continuously supplied. Instead, the data communication circuit 229 is powered by the operation power provided by the regulator 222c while a data signal is detected, so as to enable the data communication circuit 229 to selectively perform the data communication with the external device 210 by the secondary coil 221 only when data exists for communication.

Further, the communication signal detector 224, when it gets out of the shutdown mode, detects a communication signal as well as the induction of an induced electromotive force in the secondary coil 221 and rectifies a sinusoidal waveform of power signal from the resonator 222a to temporarily supply the electric power to the control unit 225. The temporary supply of the electric power by the communication signal detector 224 to the control unit 225 indicates the occurrence of communication with the external device 210 by magnetic coupling and it causes the control unit 225 to awake from the shutdown state.

In response to the temporary power supply, the control unit 225 turns on the switch 227 to allow the supply of electric power of the battery 223b to the control unit 225 and related elements. In this way, with the assistance of the communication signal detector 224, the control unit 225 turns on the switch 227 in response to an occurrence of a data communication while no electric power is provided from the battery 223b.

When a data communication is performed between the external device 210 and the implantable medical device 220 by the resonator 222a, the communication signal detector 224 detects a data signal which has been demodulated by the data communication circuit 229. Upon detecting the data signal, the communication signal detector 224 notifies to the control unit 225 that a data communication between the external device 210 and the implantable medical device 220 is being performed. In response to the notification, the control unit 225 enables the second regulator 228. Then, the electric power from the regulator 222c can be supplied to the data communication circuit 229 by the second regulator 228.

While a data signal is not detected by the communication signal detector 224, the second regulator 228 is disabled by the control unit 225 and the data communication circuit 229 is unable to receive electric power by the second regulator 228.

Meanwhile, when a data signal provided by the data communication circuit 229 during the communication with the external device 210 includes a data transmission termination signal indicating that the external device 210 terminates its data transmission, the control unit 225 disables the second regulator 228 as the control unit 225 identifies that the communication data signal includes no more data.

When the data signal provided during the communication with the external device includes a shutdown command for the medical device, the control unit 225 may shut down the entire medical device by disabling the second regulator 228 and then turning off the switch 227.

According to the present disclosure, the implantable medical device shuts off the power supply dedicated to a data communication circuit responsible for the data communication when detecting no data communication with an external terminal, and responsive to an electric power signal induced between the primary coil in the external terminal and the secondary coil in the implantable medical device for converting and supplying the same signal into a DC power for operating the data communication circuit, to thereby implement a low power consumption design of the implantable medical device.

In order to implement an even lower power consumption design of the implantable medical device in the present disclosure, while detecting no data communication with an external terminal, the implantable medical device shuts off the power supply dedicated to the data communication circuit and to the control unit and is responsive to a detection of a communication signal induced from a primary coil in the external terminal to a secondary coil in the implantable medical device for supplying the control unit and data communication circuit with an operative battery power in the implantable medical device and responsive to no detection of such communication signal for interrupting the operative battery power to the control unit and data communication circuit.

Although exemplary embodiments of the present disclosure have been described for illustrative purposes, those skilled in the art will appreciate that various substitutions, modifications and variations are possible, without departing from the technical ideas of the disclosure.

The invention claimed is:

1. An implantable medical device interworking with an external terminal having a primary coil, the implantable medical device comprising;
    a secondary coil configured to receive an RF signal from the external terminal by an induction of an induced electromotive force by magnetic coupling between the primary coil and the secondary coil, the RF signal including a power signal for energizing the implantable medical device and a data signal generated upon modulation of the power signal for use in controlling the implantable medical device;
    a power processing block configured to convert the received power signal into a DC power to be used by the implantable medical device;
    a charge unit configured to charge a battery with the DC power supplied from the power processing block;
    a communication signal detector configured to detect the data signal;
    a data communication circuit configured to be energized by the DC power supplied from the power processing block while the data signal is detected and to demodulate a modulated data; and
    a control unit configured to be energized by an operation power supplied from the battery, to control the implantable medical device according to a demodulated data signal, and to selectively connect or disconnect the data communication circuit from the power processing block depending on the presence of the data signal detected by the communication signal detector.

2. The implantable medical device of claim 1, wherein the power processing block comprises:
    a resonator configured to generate the RF signal from the induced electromotive force;
    a rectifier configured to rectify an AC power by the RF signal into the DC power; and
    a regulator configured to regulate a rectified DC power and supply the rectified DC power to the data communication circuit and the battery of the charge unit.

3. The implantable medical device of claim 1, further comprising:
    a first regulator configured to regulate the operation power supplied from the battery and provide a regulated operation power to the control unit; and
    a second regulator configured to regulate the rectified DC power supplied by the power processing block and supply a regulated DC power to the data communication circuit.

4. The implantable medical device of claim 3, wherein the control unit enables the second regulator in response to detection of the data signal supplied from the communication signal detector.

5. The implantable medical device of claim 1, further comprising a switch disposed between the control unit and the charge unit to be turned on/off according to a control of the control unit.

6. The implantable medical device of claim 5, wherein the communication signal detector is further configured to generate the DC power by rectifying the power signal when the induced electromotive force is generated, and the control unit is awakened by the DC power and is operable to turn on the switch.

7. A power control method for an implantable medical device, comprising:
    detecting an RF signal induced by magnetic coupling from a primary coil provided at an external terminal to a secondary coil provided at the implantable medical device, the RF signal including a power signal for energizing the implantable medical device and a data signal generated upon modulation of the power signal for use in controlling the implantable medical device;
    supplying a control unit with an operation power from a battery of the implantable medical device;
    in response to a detection of the data signal, supplying a data communication circuit for communicating with the external terminal with a DC power from a power processor after a conversion from the RF signal; and cutting off a power supply to the data communication circuit in the absence of the detection of the data signal.

8. The power controlling method of claim 7, wherein the operation power is regulated by a regulator.

* * * * *